United States Patent [19]

Takata et al.

[11] Patent Number: 4,954,603

[45] Date of Patent: Sep. 4, 1990

[54] EPOXY RESIN

[75] Inventors: Toshimasa Takata, Ichihara; Kenichi Mizuno, Iwakuni, both of Japan

[73] Assignee: Mitsui Petrochemical Industries, Ltd., Tokyo, Japan

[21] Appl. No.: 362,289

[22] Filed: Jun. 6, 1989

Related U.S. Application Data

[60] Continuation-in-part of Ser. No. 30,340, Mar. 26, 1987, abandoned, and a continuation-in-part of Ser. No. 227,773, Aug. 3, 1988, Pat. No. 4,894,432, which is a division of Ser. No. 916,099, Oct. 7, 1986, Pat. No. 4,778,936.

[30] Foreign Application Priority Data

Oct. 8, 1985 [JP] Japan ............................. 60-224305
Dec. 20, 1985 [JP] Japan ............................. 60-237288

[51] Int. Cl.$^5$ ..................... C08G 59/24; C07D 303/12
[52] U.S. Cl. ..................... 528/98; 528/102; 549/560
[58] Field of Search ............... 528/98, 102; 549/560

[56] References Cited

U.S. PATENT DOCUMENTS

| | | | |
|---|---|---|---|
| 3,787,451 | 1/1974 | Mah .................................. | 528/98 X |
| 4,394,496 | 7/1983 | Schrader ............................. | 528/98 |
| 4,604,317 | 8/1986 | Berman et al. ..................... | 528/98 X |
| 4,672,103 | 6/1987 | Wang et al. ........................ | 528/98 |
| 4,684,700 | 8/1987 | Wang et al. ........................ | 528/98 X |
| 4,759,978 | 7/1988 | Takata ............................... | 528/98 X |
| 4,764,580 | 8/1988 | Martin et al. ....................... | 528/98 |
| 4,783,363 | 11/1988 | Berman et al. ..................... | 528/98 |

*Primary Examiner*—Earl Nielsen
*Attorney, Agent, or Firm*—Sherman and Shalloway

[57] ABSTRACT

Disclosed is a heat-resistant flame-retardant epoxy resin composition comprising a halogen-containing epoxy resin obtained by reacting a trifunctional epoxy compound having a specific structure with a halogenated bisphenol in the presence of a catalyst. Furthermore, a novel specific trifunctional epoxy compound is disclosed, which is valuably used for the production of the above-mentioned halogen-containing epoxy resin.

15 Claims, 2 Drawing Sheets

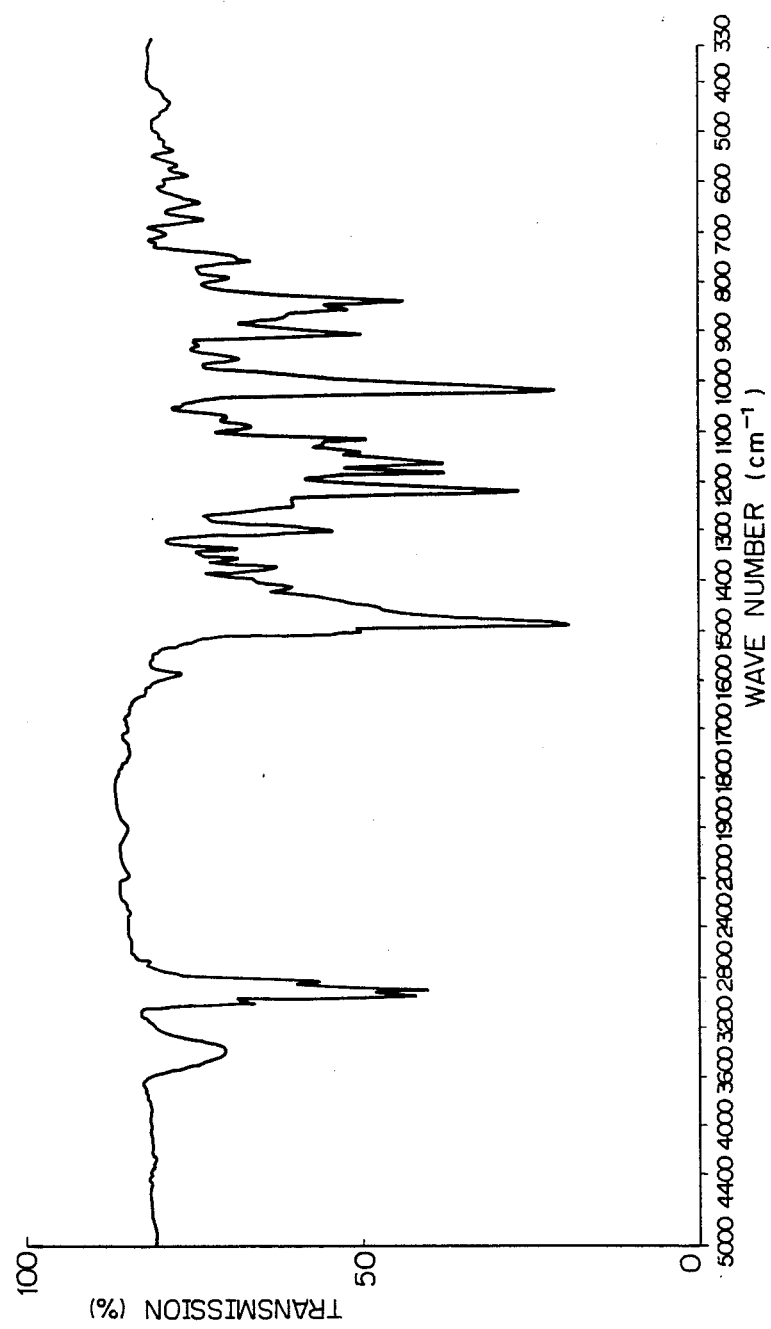

EPOXY RESIN

This application is a continuation-in-part of copending application Ser. No. 030,340, filed Mar. 26, 1987, now abandoned, and is also a continuation-in-part of copending application Ser. No 227,773, filed Aug. 3, 1988, now U.S. Pat. No. 4,894,432, issued Jan. 16, 1990, which in turn is a division of Ser. No. 916,099, filed Oct. 7, 1986 now U.S. Pat. No. 4,778,936, issued Oct. 18, 1988.

BACKGROUND OF THE INVENTION

(1) Field of the Invention

The present invention relates to an epoxy resin composition. More particularly, the present invention relates to an epoxy resin composition excellent in the heat resistance and flame retardancy, which is obtained by reacting a specific trifunctional epoxy compound with a halogenated bisphenol. Furthermore, the present invention relates to a novel epoxy resin excellent in the heat resistance and mechanical properties.

(2) Description of the Prior Art

Compositions formed by incorporating a curing agent such as an aromatic polyamine, an aliphatic polyamine, a polyamide-amine, an amine adduct, dicyandiamide, an acid anhydride or a phenol-novolak resin into an epoxy resin have been used as adhesives, paints, molding materials and casting materials. Moreover, it is known that a varnish is formed by dissolving such a composition in a solvent, a reinforcing substrate is impregnated or coated with this varnish and the impregnated or laminated reinforcing substrate is used for molding a laminated plate.

Recently, in the electrical and electronic fields, with required reduction of the size and required increase of the precision, improvement of the heat resistance is eagerly desired in adhesives, insulating paints, sealants and laminated plates for electronic parts for enhancing the reliability at high-temperature applications. More specifically, an adhesive, paint, sealant or laminated plate prepared by using a commercially available bisphenol A type epoxy resin is generally low in the heat distortion temperature or electrical insulating property and, therefore, the reliability is poor.

Furthermore, a high flame retardancy is required for materials used in the electrical or electronic field. As the flame-retardant epoxy resin used as a laminated plate (printed circuit substrate comprising a laminate of a glass cloth and an epoxy resin), there is known, for example, a linear epoxy resin obtained by reacting a bisphenol A type epoxy resin such as a liquid bisphenol A type epoxy resin having an epoxy equivalent of about 190 with tetrabromobisphenol A. When this linear epoxy resin is cured with, for example, dicyandiamide which is a curing agent used for formation of a laminated plate and having a high general-purpose property, the glass transition temperature (Tg) of the cured product (the bromine content is 20 to 22% by weight) is as low as 120° to 130° C. If a large amount of a polyfunctional epoxy resin such as o-cresol-novolak epoxy resin or a phenol-novolak epoxy resin is added to the above epoxy resin so as to increase the heat resistance of the cured product, the flame retardancy is reduced and the moldability becomes insufficient and, therefore, the amount added of the polyfunctional epoxy resin is restricted.

As is apparent from the foregoing description, in the known epoxy resins, the heat resistance and flame retardancy are properties contradictory to each other, and an epoxy resin excellent in both the heat resistance and flame retardancy is not known. In the electronic field where high performance is required, in order to improve the reliability of a cured product at high temperatures, development of an epoxy resin excellent in both the heat resistance and flame retardancy is eagerly desired.

A cured product formed from a polyfunctional epoxy resin such as an o-cresol-novolak epoxy resin or a phenol-novolak resin has a high flexural modulus and hence, is hard and brittle and, therefore, the cured product is poor in the mechanical properties and cracking is readily caused by a thermal shock. Accordingly, development of an epoxy resin excellent in both the heat resistance and mechanical properties is eagerly desired.

SUMMARY OF THE INVENTION

We found that an epoxy resin composition obtained by reacting a trifunctional epoxy compound having a specific structure with a halogenated bisphenol A in the presence of a catalyst has excellent heat resistance and excellent flame retardancy in combination. It also was found that a trifunctional epoxy resin having a specific structural formula has excellent heat resistance and excellent mechanical properties in combination.

It is a primary object of the present invention to provide a novel epoxy resin composition which can be formed into an insulating paint, sealant or molded product excellent in both the heat resistance and flame retardancy by curing.

Another object of the present invention is to provide a novel epoxy resin composition which can be formed into a laminated plate having an improved reliability of the mechanical strength or electrical insulating property at high temperatures by curing.

Still another object of the present invention is to provide a novel epoxy resin which can be formed into a paint, sealant or molded product excellent in the heat resistance and mechanical characteristics and having a high resistance to cracking by a thermal shock by curing.

In accordance with one fundamental aspect of the present invention, there is provided a heat-resistant flame-retardant epoxy resin composition comprising a halogen-containing epoxy resin obtained by reacting (A) a trifunctional epoxy compound represented by the following general formula (I):

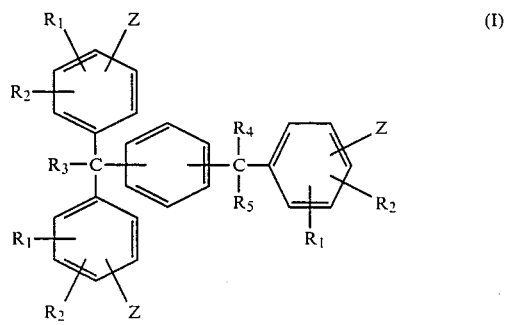

wherein $R_1$ and $R_2$ stand for a hydrogen atom, an alkyl group having 1 to 12 carbon atoms, an aryl group or a cycloalkyl group having 3 to 6 carbon atoms, $R_3$ stands for a hydrogen atom or an alkyl group having 1 to 10 carbon atoms, $R_4$ and $R_5$, independently, stand for a hydrogen atom or an alkyl group having 1 to 4 carbon atoms, and Z stands for a group represented by the following general formula (II):

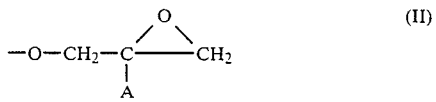

in which A stands for a hydrogen atom or a methyl group, or a combination of said trifunctional epoxy compound and a difunctional epoxy compound obtained by condensation of a bisphenol with an epihalohydrin with (B) a halogenated bisphenol in the presence of a catalyst.

In accordance with another fundamental aspect of the present invention, there is provided a trifunctional epoxy compound represented by the following general formula (IX):

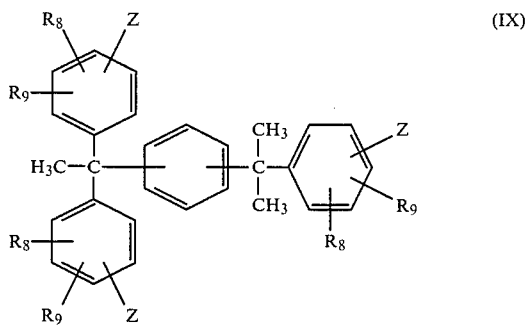

wherein $R_8$ and $R_9$ stand for a hydrogen atom, a halogen atom, a lower alkyl group having 1 to 4 carbon atoms or a lower alkoxy group having 1 to 4 carbon atoms, the groups $R_8$ and $R_9$ bonded to the respective phenyl groups may be the same or different, and Z stands for a group represented by the following general formula (II):

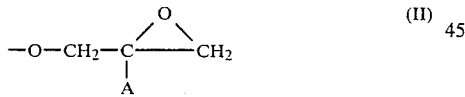

in which A stands for a hydrogen atom or a methyl group.

Since the epoxy resin of the present invention is an epoxy resin obtained by reacting the above-mentioned specific trifunctional epoxy compound with a halogenated bisphenol, as is apparent from comparison of application examples given hereinafter with comparative application examples given hereinafter, a cured product prepared from the epoxy resin of the present invention has a much higher heat resistance than that of a cured product prepared from a known flame-retardant epoxy resin, and since the epoxy resin of the present invention contains a halogen, the cured product shows an excellent flame retardancy.

Accordingly, if the epoxy resin of the present invention is laminated with, for example, a glass cloth and is cured, there can be obtained a laminate which is excellent in both the heat resistance and flame retardancy and has an improved reliability at high temperatures and which is very valuable as an electronic part. Moreover, when the novel epoxy resin of the present invention is cured, there can be provided a cured product having a higher flexural strength and a lower flexural modulus than those of a cured product of a conventional epoxy resin and also having a heat distortion temperature higher than 230° C.

Therefore, according to the present invention, there is provided an epoxy resin which gives a cured product having a high reliability even at high temperature when the epoxy resin is used as an adhesive, a paint, a sealant, a molding material, a varnish or a material for formation of a laminated plate.

Although the epoxy resin is derived from a trifunctional epoxy compound, the epoxy resin has a substantially linear, gel-free structure such that the epoxy resin is completely soluble in an organic solvent such as methylethylketone, and the epoxy resin of the present invention is advantageous in that the handling and processing properties are very good when the epoxy resin is used in various fields.

BRIEF DESCRIPTION OF THE DRAWINGS

FIG. 2 shows an infrared absorption spectrum of an epoxy resin obtained in Example 2, which is a novel compound included within the scope of the trifunctional epoxy compound of the present invention.

DETAILED DESCRIPTION OF THE PREFERRED EMBODIMENTS

Figure 1:
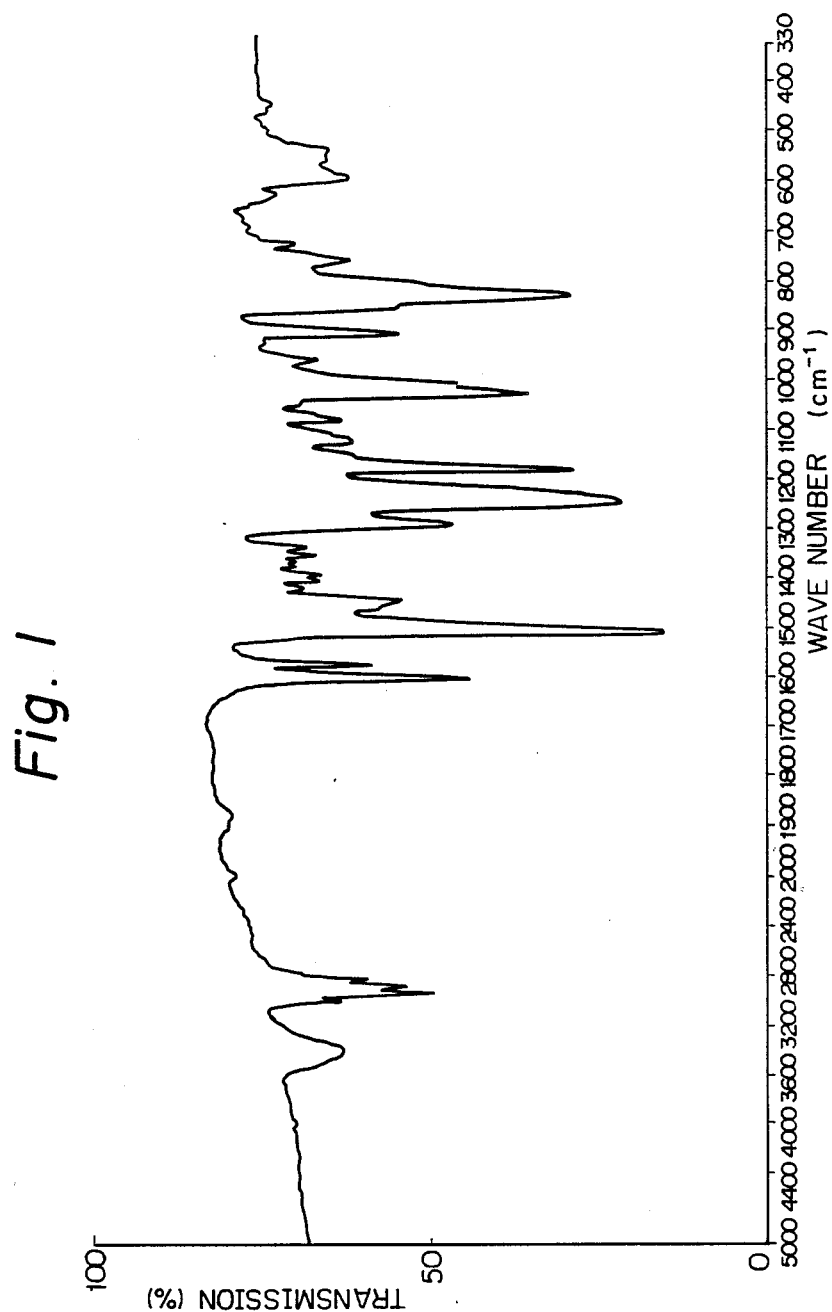
FIG. 1 shows an infrared absorption spectrum of an epoxy resin obtained in Example 1, which is a novel compound included within the scope of the trifunctional epoxy compound of the present invention.

The trifunctional epoxy compound used for obtaining the epoxy resin of the present invention is represented by the above-mentioned general formula (I), and it is preferred that this trifunctional epoxy compound be a compound represented by the following formula (XIII):

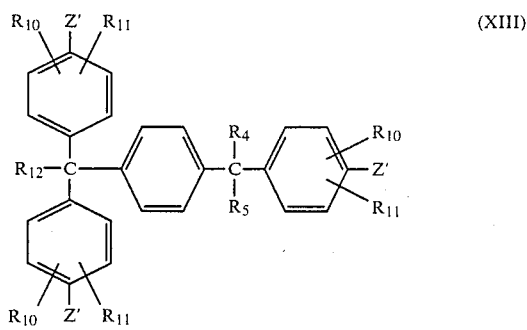

wherein Z' stands for a glycidoxy group, and $R_{10}$, $R_{11}$, $R_{12}$, $R_4$ and $R_5$ each, independently, stand for a hydrogen atom or an alkyl group having 1 to 4 carbon atoms. It is especially preferred that at least one of $R_4$ and $R_5$ are alkyl, and most preferably both of $R_4$ and $R_5$ are alkyl, such as methyl, ethyl or propyl. $R_{12}$ is also preferably alkyl, such as methyl.

As preferred examples of the trifunctional epoxy compound represented by the general formula (I), there can be mentioned 1-{α-methyl-α-(4'-glycidoxyphenyl)ethyl}-4-{α',α'-bis(4''-glycidoxyphenyl)ethyl}benzene, 1-{α-methyl-α-(2'-methyl-4'-glycidoxy-5'tert-butylphenyl)ethyl}-4-{α',α'-bis(2''-methyl-4''-glycidoxy-5''- tert-butylphenyl)ethyl}benzene, 1{α-methyl-α-(3′,5′-dimethyl-4′-glycidoxyphenyl)ethyl}-4-{α′,α′,-bis(3″,5″-dimethyl-4″-glycidoxyphenyl)ethyl}benzene, 1-{α-methyl-α-(3′-tert-butyl-4′-glycidoxyphenyl)ethyl}-4-{α′,α′-bis(3″-tert-butyl-4″-glycidoxyphenyl)ethyl}benzene, 1-{α-methyl-α-(3′-methyl-4′-glycidoxy-5′-tert-butylphenyl)ethyl}-4-{α′,α′-bis(3″-methyl-4″-glycidoxy-5″-tert-butylphenyl)ethyl}benzene and 1-{α-methyl-α-(2′,5′-dimethyl-4′-glycidoxyphenyl)ethyl}-4-{α′,α′-bis(2″,5″-dimethyl-4″-glycidoxyphenyl)ethyl} benzene.

Among these trifunctional epoxy compounds, those represented by the general formula (IX) are epoxy compounds not disclosed in any literature reference. In the general formula (IX), it is preferred that the group Z be bonded to the para-position of the phenyl group and $R_8$ and $R_9$ should stand for a hydrogen atom or an alkyl group having 1 to 4 carbon atoms.

The trifunctional epoxy compound represented by the general formula (I) is prepared, for example, by etherifying a tris-phenol compound represented by the following general formula (XI):

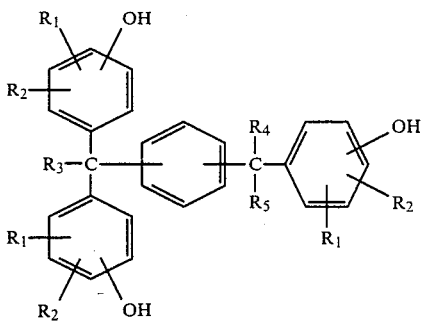

(XI)

wherein $R_1$, $R_2$, $R_3$, $R_4$, and $R_5$ are as defined above, with an epihalohydrin or a β-methylepihalohydrin, preferably epichlorohydrin or β-methylepichlorohydrin, in the presence of an appropriate etherifying catalyst, and dehydrohalogenating the etherification product.

The tris-phenol compounds of formula (XI) can be prepared by the method disclosed in our copending application Ser. No. 227,773, filed Aug. 3, 1988, and its parent application Ser. No. 916,099, filed Oct. 7, 1986, now issued as U.S. Pat. No. 4,778,099, the disclosure of which is incorporated herein in its entirety by reference thereto. For example, the tris-phenol compounds can be prepared by the reaction between an alkenyl substituted benzaldehyde or acetophenone with a phenolic compound. The alkenyl substituted benzaldehyde or acetophenone may, for example, be a compound of the formula (XVIII):

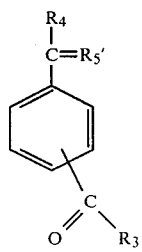

(XVIII)

wherein $R_3$ and $R_4$ are as defined above and $R'_5$ is alkylene of 1 to 4 carbon atoms. The phenolic compound may, for example, be a compound of the formula (XIX):

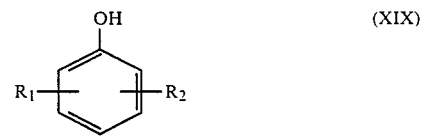

(XIX)

where $R_1$ and $R_2$ are as defined.

For instance, the tris-phenol compound of formula (XI′), in which each of $R_3$, $R_4$ and $R_5$ are methyl, can be prepared by reacting isopropenyl acetophenone (R′$_5$ is methylene) with a phenolic compound of formula (V) according to the following scheme:

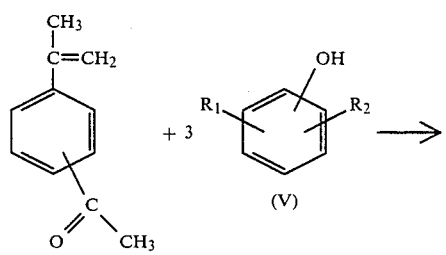

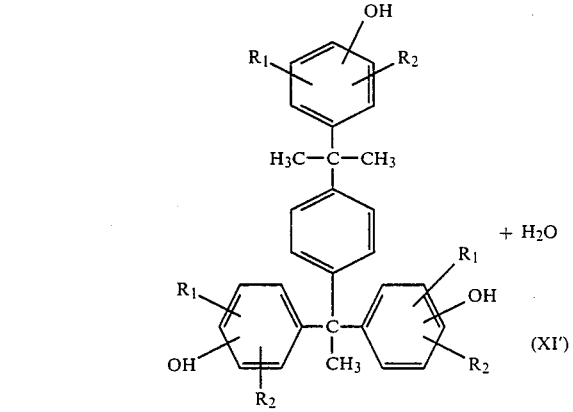

(XI′)

wherein $R_1$ and $R_2$ are as defined above.

The isopropenylacetophenone may be m-isopropenylacetophenone, p-isopropenylacetophenone or a mixture thereof.

Examples of the phenolic compounds of formula (V) usable in this reaction include, for instance, phenol, o-cresol, m-cresol, p-cresol, 2,6-xylenol, o-methoxyphenol, m-methoxyphenol, 2,6-diethylphenol, o-, m- or p-ethylphenol, o-, m- or p-propylphenol, o-, m- or p-butylphenol or mixtures thereof. When a mixture of the above phenolic compounds is used, it is possible to obtain a compound wherein the $R_1$'s and $R_2$'s in the triphenol compound (XI) are different from each other.

A triphenol type compound wherein $R_1$ and/or $R_2$ is a halogen in the above formula can be produced by using a phenolic compound in which the nucleus is substituted with a halogen as the starting material, or alternatively, it can be produced in some cases by halogenating a triphenol prepared from a phenolic compound having no halogen substituents.

The above reaction between isopropenyl acetophenone (or other aromatic aldehyde) and a phenol can be carried out by, preferably, mixing an excess (e.g. 1.5 to 10 times) of the stoichiometric amount of a phenolic compound and an acid such as hydrogen chloride, sulfuric acid, hydrogen bromide, p-toluenesulfonic acid and cationic ion exchange resins as the catalyst, and adding isopropenyl acetophenone dropwise into the mixture obtained The preferable amount of the catalyst is 0.03 to 1.0 parts by weight, based on 1.0 part by weight of the isopropenyl acetophenone. During this reaction, methylmercaptan or mercaptoacetic acid may be added, preferably up to 0.3 parts by weight, more preferably 0.01 to 0.3 parts by weight, based on 1.0 part by weight of the isopropenyl acetophenone, as a cocatalyst into the reaction system, if desired.

This reaction is carried out generally at a temperature range of from 40° C. to 80° C. at atmospheric pressure or elevated pressure (preferably 1 to 20 atm). The preferable reaction time is 1 to 100 hours.

For separation and purification of the triphenol compound, which is the desired compound, from the reaction mixture, general methods such as extraction, concentration, crystallization, etc., can be used.

The structure of the triphenol type compound obtained is determined by, for example, mass spectrometry, proton nuclear magnetic resonance and melting point.

If the tris-phenol compound is reacted with an epihalohydrin or a β-methylepihalohydrin, not only the trifunctional epoxy compound represented by the general formula (I) but also a polyfunctional epoxy compound such as a tetra-functional epoxy compound represented by the following general formula (XII):

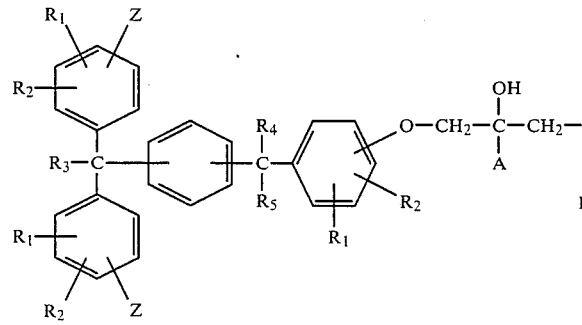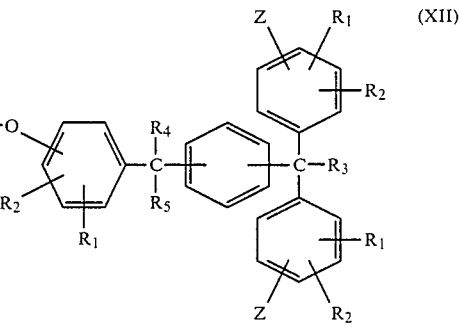

(XII)

wherein $R_1$, $R_2$, $R_3$, $R_4$, $R_5$, Z, and A are as defined above, is formed. In the present invention, even if a polyfunctional epoxy compound mixture comprising the trifunctional epoxy compound represented by the general formula (I) and other polyfunctional epoxy compound obtained by reacting the trisphenol compound represented by the general formula (XI) with an epihalohydrin or a β-methylepihalohydrin is used, a heat-resistant flame-retardant epoxy resin can be obtained by reacting this mixture with a halogenated bisphenol. Accordingly, the following description made with reference to the tri-functional epoxy compound which is the main component of the composition of the present invention will also hold good with respect to the above-mentioned polyfunctional epoxy compound mixture.

The reaction of the tris-phenol compound with the epihalohydrin or β-methylepihalohydrin can be accomplished according to various known processes. For example, there can be adopted a process in which an alkali compound, for example, an alkali metal hydroxide such as sodium hydroxide, potassium hydroxide or lithium hydroxide, preferably sodium hydroxide, is used in an amount of at least 1 mole, preferably 1.02 to 1.05 mole, per equivalent of the phenolic hydroxyl group of the tris-phenol, etherification and dehydrohalogenation are simultaneously carried out in the presence of water at a temperature of about 60° to about 90° C., the unreacted halohydrin, water and the formed salt are removed from the reaction mixture after the reaction and the trifunctional epoxy compound as the reaction product is dried and recovered.

However, a process in which etherification and dehydrohalogenation are carried out in sequence is preferred because an epoxy compound having a stable quality can be obtained.

The etherification is carried out in the presence of about 0.005 to 5 mole %, based on 1 equivalent of the phenolic hydroxyl group of the tris-phenol, of an etherifying catalyst, for example, a tertiary amine such as trimethylamine or tri-ethylamine, a tertiary phosphine such as triphenylphosphine or tributylphosphine, a quaternary ammonium salt such as tetramethyl ammonium chloride, tetramethyl ammonium bromide, tetraethyl ammonium chloride, tetraethyl ammonium bromide or choline chloride, a quaternary phosphonium salt such as tetramethyl phosphonium bromide, tetramethyl phosphonium iodide or triphenylpropyl phenylpropyl phosphonium bromide or a tertiary sulfonium salt such as benzyldibutyl sulfonium chloride or benzyldimethyl sulfonium chloride, preferably a quaternary ammonium salt.

At the etherification step, the reaction is carried out to such an extent that at least about 50%, preferably at least about 80%, of the hydroxyl group of the trisphenol be etherified. The reaction is generally conducted at a temperature of about 60° to about 110° C. for about 1 to about 12 hours. The presence of water is not preferred. If water is present, the amount of water should be controlled below 3.0% by weight.

At the subsequent dehydrohalogenation step, the reaction product obtained at the etherification step is subjected to the reaction as it is, that is, in the state where the reaction product contains the unreacted epihalohydrin. As the catalyst for the reaction, there is used the same alkali compound as used in the above-mentioned first process, for example, an alkali metal hydroxide, preferably sodium hydroxide, in an amount of at least 0.5 mole, preferably at least 0.8 mole, per equivalent of the phenolic hydroxyl group of the trisphenol. However, in order to avoid gelation or the like, the amount of the catalyst should be smaller than 1 mole per equivalent of the phenolic hydroxyl group of the tris-phenol.

It is preferred that the epihalohydrin or β-methylepihalohydrin be used in an amount of 3 to 30 moles per mole of the tris-phenol compound. From the industrial viewpoint, epichlorohydrin or β-methylepichlorohydrin is preferred as the epihalohydrin or β-methylepihalohydrin.

After completion of the reaction, removal of the unreacted epihalohydrin by distillation under reduced pressure, removal of the salt formed as the by-product by water washing or the like and, if necessary, neutralization with a weak acid such as phosphoric acid or sodium dihydrogenphosphate are carried out, and then drying is carried out to obtain the intended epoxy compound.

The trifunctional compound of the present invention is semi-solid or a solid having a softening point lower than 130° C., and the epoxy equivalent is from 154 to 380.

In view of the effect of improving the flame retardancy and the easy industrial availability, a brominated bisphenol is preferred as the halogenated bisphenol to be reacted with the trifunctional epoxy compound in the present invention. For example, tetrabromobisphenol A, tetrabromobisphenol B, tetrabromobisphenol F and 1,1-bis(3,5-dibromo-4-hydroxyphenyl)ethane are especially preferred.

In the present invention, the reaction of the trifunctional epoxy compound with the halogenated bisphenol is carried out in the presence of a catalyst in the absence of a solvent or, if necessary, in a solvent, for example, an aromatic solvent such as toluene or xylene or a ketone solvent such as methylisobutyl ketone.

Any of known catalysts customarily used for the polyaddition reaction between the epoxy group and the phenolic hydroxyl group can be used as the catalyst in the present invention. For example, there can be mentioned basic catalysts such as sodium hydroxide and sodium carbonate, quaternary ammonium salt catalysts such as tetra-alkyl ammonium halides and aralkyl-trialkyl ammonium halides and phosphorus type catalysts such as triphenylphosphine and ethyltriphenyl phosphonium halides. It is preferred that the catalyst be used in an amount of about 10 to about 400 ppm based on the used trifunctional epoxy compound The above reaction can be carried out at a temperature of about 120° to about 200° C. under atmospheric pressure for about 3 to about 20 hours with stirring in the molten state or solution state.

In the above reaction, a difunctional epoxy compound such as a bisphenol A type epoxy resin, a bisphenol F type epoxy resin or 1,1-bis(glycidoxyphenyl)ethane may be present in the reaction system. In the epoxy resin composition of the present invention obtained by reacting the trifunctional epoxy compound with the halogenated bisphenol, as the halogen content is high, the softening point tends to be too high. However, if the above-mentioned difunctional epoxy compound is used in combination with the trifunctional epoxy compound, the softening point of the obtained epoxy resin can be reduced without degradation of the flame retardancy. Accordingly, the amount used of the difunctional epoxy compound can be appropriately adjusted according to the halogen content of the epoxy resin composition of the present invention and the desired halogen content. However, in order to improve the glass transition temperature of the cured product obtained from the epoxy resin composition of the present invention over that of a cured product obtained from a known epoxy resin, it is preferred that the weight ratio of the trifunctional epoxy compound to the difunctional epoxy compound be in the range of from 50/50 to 90/10, especially from 60/40 to 80/20.

The reaction ratio of the epoxy compound to the halogenated bisphenol is appropriately selected according to the desired halogen content in the epoxy resin composition obtained by the reaction. However, it is generally preferred that the reaction ratio be selected so that the halogen content in the epoxy resin composition of the present invention obtained by the reaction is 5 to 30% by weight, especially 10 to 25% by weight, particularly especially 15 to 20% by weight. If the halogen content in the epoxy resin composition is too low and below the above-mentioned range, no sufficient flame retardancy can be attained.

In order to attain the objects of the present invention, it is preferred that the epoxy equivalent of the final epoxy resin be 300 to 2000, especially 300 to 1000.

The epoxy resin composition of the present invention comprises a polymer represented by the following general formula (XVI), though the general formula is not particularly critical:

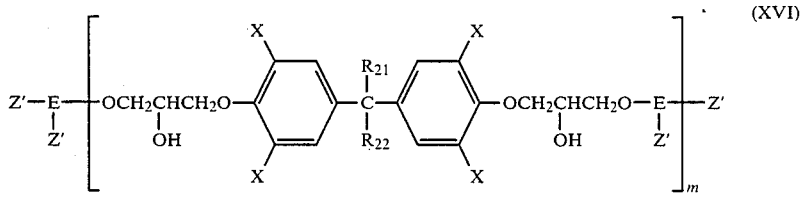

(XVI)

wherein Z' stands for a glycidoxy group, $R_{21}$ and $R_{22}$ stand for a hydrogen atom or an alkyl group having 1 to 4 carbon atoms, X stands for a halogen atom, E stands for a group represented by the following formula (XIII'):

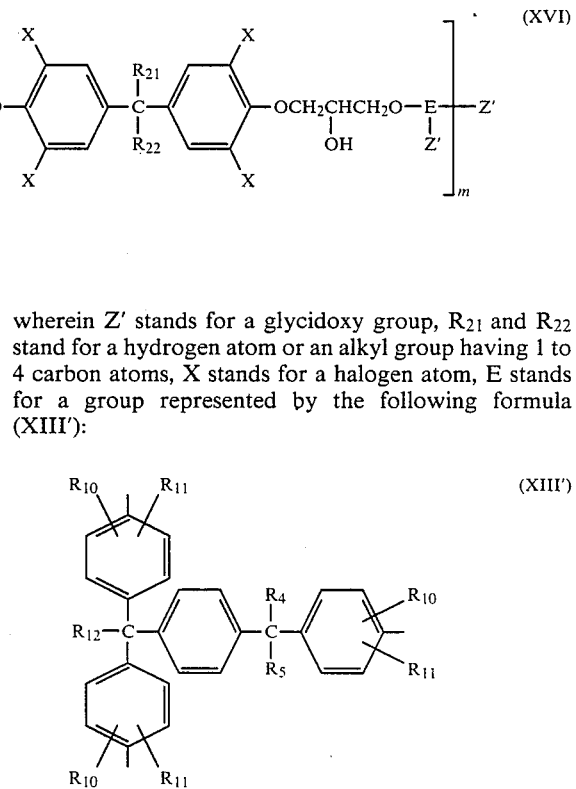

(XIII')

in which $R_{10}$, $R_{11}$, $R_{12}$, $R_4$ and $R_5$, each independently, stand for a hydrogen atom or an alkyl group having 1 to 4 carbon atoms and m is an integer of at least 1.

Moreover, the epoxy resin composition derived from the combination of the trifunctional epoxy compound and the difunctional epoxy compound comprises a copolymer represented by the following general formula (XVII):

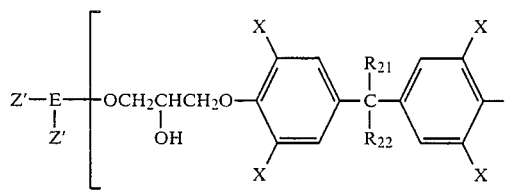 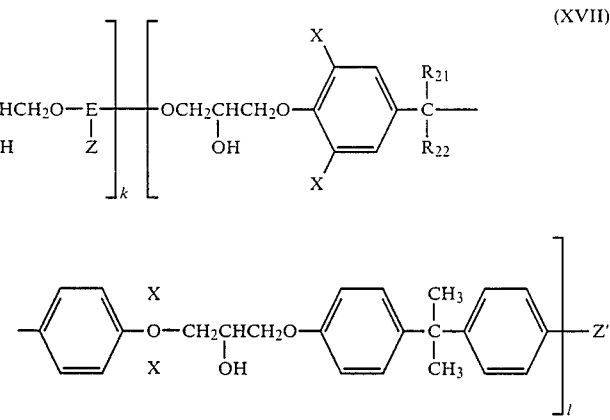

(XVII)

wherein Z' stands for glycidoxy group, $R_{21}$ and $R_{22}$ stand for a hydrogen atom or an alkyl group having 1 to 4 carbon atoms, X stands for a halogen atom, E stands for a group represented by the following formula (XIII'):

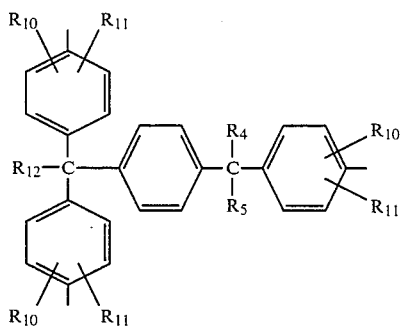

(XIII')

in which $R_{10}$, $R_{11}$, $R_{12}$, $R_4$ and $R_5$, each independently, stand for a hydrogen atom or an alkyl group having 1 to 4 carbon atoms, k is 0 or an integer of at least 1, l is an integer of at least 1, and k and l are selected so that the halogen-containing epoxy resin has an epoxy equivalent of 300 to 2000 and a halogen content of 5 to 30% by weight.

The epoxy resin composition of the present invention may further comprise a known epoxy resin such as a phenolnovolak type epoxy resin or an o-cresol-novolak type epoxy resin, so far as the attainment of the objects of the present invention is not hindered.

In addition to the foregoing components, the epoxy resin composition of the present invention may comprise an unreactive diluent such as a phthalic acid ester or an ether or ester of a glycol, a reactive diluent such as a long-chain alkylene oxide, butylglycidyl ether, phenylglycidyl ether or p-butylphenyl-glycidyl ether, a filler such as calcium carbonate, clay, asbestos, silica, mica, quartz powder, aluminum powder, graphite, titanium oxide, alumina, iron oxide, glass powder or glass fiber, and a colorant such as carbon black, Toluidine Red, Hansa Yellow, Phthalocyanine Blue or Phthalocyanine Green.

When the epoxy resin composition of the present invention is actually used, a known curing agent for an epoxy resin, for example, an aliphatic amine, an aromatic amine, an amine adduct, dicyandiamide, a phenolnovolak resin, an o-cresolnovolak resin or an acid anhydride is incorporated into the epoxy resin composition, and the composition is used for the production of an electrically insulating paint, a molding material, a sealant, a laminated plate and the like.

The amount used of the curing agent is changed according to the kind of the curing agent. For example, in case of a polyamine, the amount used of the polyamine as the curing agent is determined based on the ratio between the epoxy equivalent and the active hydrogen equivalent. A curing promotor can be used according to need.

When the epoxy resin composition is used for a paint, a general-purpose colorant (pigment), a filler, a solvent, a defoamer and the like are incorporated into the epoxy resin composition, and various fillers can be incorporated for the production of sealants. When the epoxy resin composition is used for the production of a laminated plate, a varnish is generally formed by dissolving the epoxy resin composition in an aromatic hydrocarbon such as toluene or xylene or a ketone type solvent such as acetone, methylethylketone or methylisobutylketone. A reinforcing substrate such as a glass cloth, carbon fiber, glass fiber, paper, asbestos, polyester fiber or aromatic polyamide fiber (such as a product marketed under the tradename of "Kevlar") is impregnated with the so-formed varnish to form a prepreg, and the prepregs are heat-pressed to obtain a laminated plate.

The trifunctional epoxy compound represented by the general formula (IX) may be mixed with other epoxy resin, a reactive diluent, a filler, a colorant and the like according to need, so far as the characteristics are not degraded, as described hereinbefore with respect to the heat-resistant flame-retardant epoxy resin composition, and the resulting composition is mixed with a curing agent and, if necessary, a curing promotor, and is used for the production of an electrically insulating paint, a sealant, a molding material, an adhesive, a material for formation of a laminated plate and the like.

The present invention will now be described in detail with reference to the following examples that by no means limit the scope of the invention.

Preparation of typical tris-phenol compounds of formula (XI) are shown in the following Referential Examples. These preparations were carried out at atmospheric pressure.

REFERENTIAL EXAMPLE 1

Preparation of 1-{α-methyl-α-(4'-hydroxyphenyl)ethyl}-4-{α',α'-bis(4''-hydroxyphenyl)ethyl}benzene from p-isopropenylacetophenone and phenol:

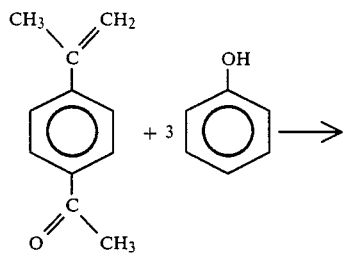

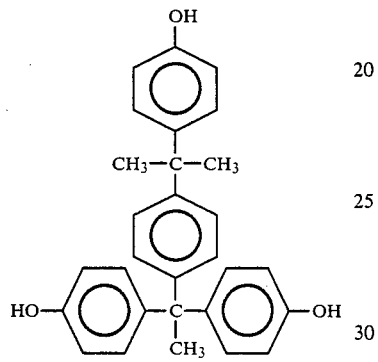

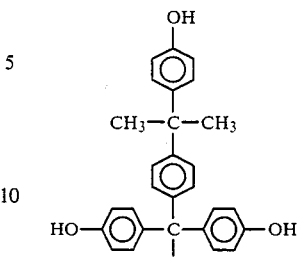

FD-MS (mass spectrometry)
M+ = 424
¹H-NMR
(proton nuclear magnetic resonance)
(CD₃OD Solution)
δ = 1.60, 6H, S
δ = 2.02, 3H, S
δ = 4.9, 3H, S
δ = 6.6–7.2, 16H, m

REFERENTIAL EXAMPLE 2

Preparation of 1-{α-methyl-α-(4'-hydroxyphenyl)ethyl}-3-{α',α'-bis(4''-hydroxyphenyl)ethyl}benzene from m-isopropenylacetophenone and phenol:

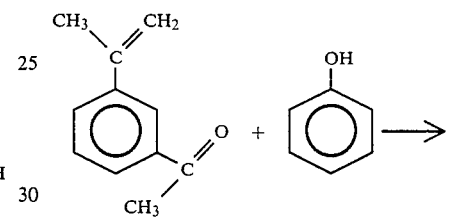

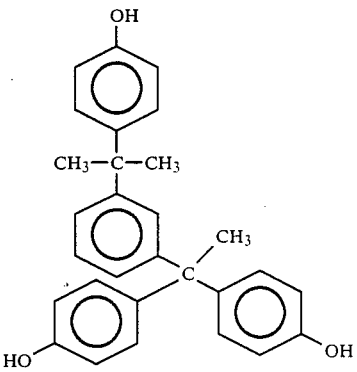

(1) Into a 500 ml round-bottomed flask equipped with a stirrer, a dropping funnel, a thermometer, a reflux condenser and a gas blowing pipe, were charged 194 g of phenol and 4 g of 15 weight % aqueous methylmercaptan sodium salt solution, and after heating to 40° C., dry hydrogen chloride gas was blown through a gas charging pipe under stirring until the system was internally saturated. Subsequently, a mixture of 32 g of p-isopropenylacetophenone and 32 g of phenol was added dropwise through a dropping funnel over 2 hours. During this period, the reaction temperature was maintained at 40° to 43° C., and the blowing of dry hydrogen chloride gas was also continued. After completion of the dropwise addition, stirring was continued at a temperature of 40° to 43° C. while blowing, little by little, dry hydrogen chloride gas for an additional 8 hours.

(2) The reaction mixture obtained was left to stand overnight at room temperature, then added with 1200 g of toluene and 600 g of 3 weight % aqueous sodium hydrogen carbonate solution, and the mixture was stirred at 80° C. for 30 minutes, followed by cooling of the whole mixture as such to room temperature. The precipitated crystals were separated by a centrifugal machine, and the crystals were washed with toluene and then with H₂O. Further, the crystals were dissolved in a heated solvent mixture of methyl isobutyl ketone-toluene, washed with water and then cooled to precipitate crystals again. The crystals were separated to obtain 70.8 g of white crystals melting at 222° to 225° C. The crystals were identified from the results of mass spectrometry and proton nuclear magnetic resonance to be 1-{α-methyl-α-(4'-hydroxyphenyl)ethyl}-4-{α',α'-bis(4'-hydroxyphenyl)ethyl}benzene having the following formula:

(1) The reaction was carried out according to the same procedure as described in Example 1(1) except for using misopropenylacetophenone in place of p-isopropenylacetophenone.

(2) The reaction mixture obtained was dissolved in 640 g of toluene, washed with 3 weight percent aqueous NaHCO₃ solution and then with a dilute aqueous phosphoric acid solution, followed by evaporation of the toluene and unreacted phenol under a reduced pressure. The residue obtained was recrystallized from toluene to obtain 69.3 g of white crystals. The crystals exhibited a melting point of 187° to 189° C. and were identified from the results of mass spectrometry and proton nuclear magnetic resonance to be 1-{α-methyl-α-(4'-hydroxyphenyl)ethyl}-3-{α',α'-bis(4''-hydroxyphenyl)ethyl}benzene having the following formula:

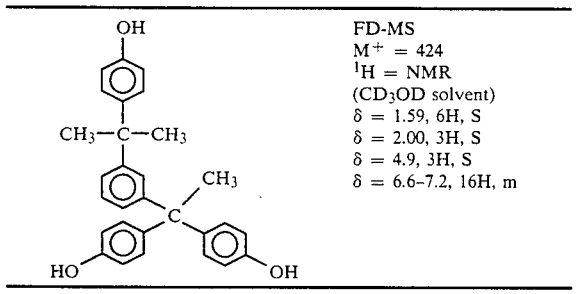

| | FD-MS<br>M+ = 424<br>$^1$H = NMR<br>(CD$_3$OD solvent)<br>δ = 1.59, 6H, S<br>δ = 2.00, 3H, S<br>δ = 4.9, 3H, S<br>δ = 6.6–7.2, 16H, m |
|---|---|

REFERENTIAL EXAMPLE 3

Preparation of 1-{α-methyl-α-(3′,5′-dimethyl-4′-hydroxyphenyl)ethyl}-4-{α′,α′-bis(3″,5″-dimethyl-4″-hydroxyphenyl)ethyl}benzene from p-isopropenylacetophenone and 2,6-xylenol:

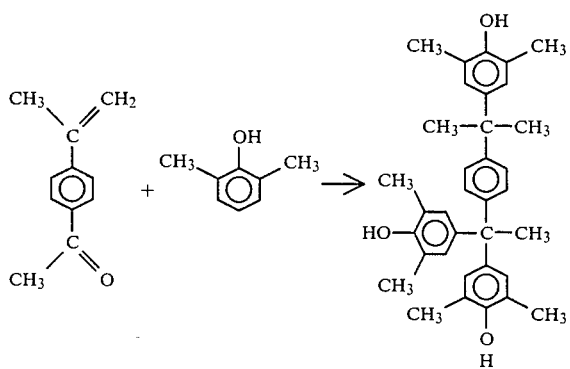

(1) Into the reactor as shown in Example 1(1) were charged 228 g of 2,6-xylenol, 5.8 g of 15 weight percent aqueous methylmercaptan sodium salt solution and 56 g of concentrated hydrochloric acid, and the mixture was heated to 50° C. Under stirring, while blowing dry hydrogen chloride gas through the gas blowing pipe, a mixture of 32 g of p-isopropenylacetophenone and 64 g of 2,6-xylenol was added dropwise over 2 hours. During this period, the reaction temperature was maintained at 46° to 48° C. After completion of the dropwise addition, stirring was continued at 46° to 48° C. while blowing dry hydrogen chloride gas for 70 hours to complete the reaction.

(2) To the reaction mixture obtained was added 400 g of toluene and the mixture was heated to 80° C. After the separated aqueous layer was removed, the oil layer was washed with 3 weight percent aqueous NaHCO$_3$ solution and then with a dilute aqueous phosphoric acid solution. After toluene and unreacted 2,6-xylenol were evaporated under a reduced pressure from the oil layer, the residue was recrystallized twice from toluene to obtain 67.1 g of white crystals The crystals exhibited a melting point of 191° to 194° C. and were identified from the results of mass spectrometry and proton nuclear magnetic resonance to be 1-{α-methyl-α-(3′,5′-dimethyl-4′-hydroxyphenyl)ether}-4-{α′,α′-bis(3″,5″-dimethyl-4″-hydroxyphenyl)ethyl}benzene having the following formula:

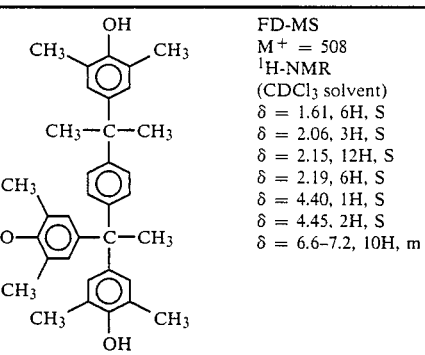

| | FD-MS<br>M+ = 508<br>$^1$H-NMR<br>(CDCl$_3$ solvent)<br>δ = 1.61, 6H, S<br>δ = 2.06, 3H, S<br>δ = 2.15, 12H, S<br>δ = 2.19, 6H, S<br>δ = 4.40, 1H, S<br>δ = 4.45, 2H, S<br>δ = 6.6–7.2, 10H, m |
|---|---|

REFERENTIAL EXAMPLE 4

Preparation of 1-{α-methyl-α-(3′-methyl-4′-hydroxyphenyl)ethyl}-4-{α′.α′bis(3″-methyl-4″-hydroxyphenyl)ethyl}benzene from p-isopropenylacetophenone and o-cresol:

(1) The reaction was carried out according to the same procedure as described in Example 1(1) except that 227 g of o-cresol was used instead of phenol.

(2) The reaction mixture obtained was dissolved in 500 g of toluene, washed with 3 weight percent aqueous NaHCO$_3$ solution and then with dilute aqueous phosphoric acid solution, followed by evaporation of the toluene and unreacted o-cresol under a reduced pressure.

The residue obtained was recrystallized from decane to obtain 69.8 g of pale yellow solids. The solid exhibited a melting point of 87° to 91° C. and was identified from the results of mass analysis and proton nuclear magnetic resonance to be 1-{α-methyl-α-(3′-methyl-4′-hydroxyphenyl)ethyl}-4-{α′,α′-bis(3′-methyl-4′-hydroxyphenyl)ethyl}benzene having the following formula:

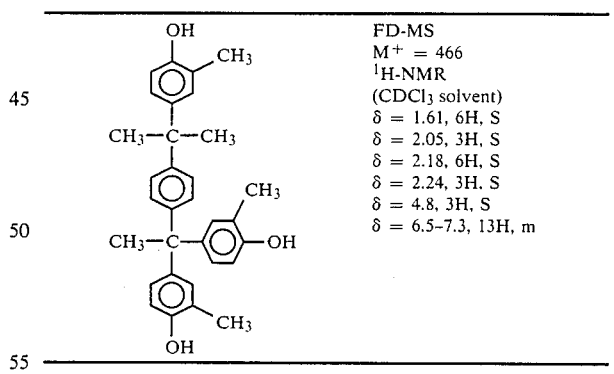

| | FD-MS<br>M+ = 466<br>$^1$H-NMR<br>(CDCl$_3$ solvent)<br>δ = 1.61, 6H, S<br>δ = 2.05, 3H, S<br>δ = 2.18, 6H, S<br>δ = 2.24, 3H, S<br>δ = 4.8, 3H, S<br>δ = 6.5–7.3, 13H, m |
|---|---|

EXAMPLE 1

A 1-liter four-neck glass flask equipped with a stirring rod and a reflux device was charged with 462.5 g of epichlorohydrin, 141.3 g of 1-{α-methyl-α-(4′-hydroxyphenyl)ethyl}-4-{α′,α′-bis(4″hydroxyphenyl)ethyl}benzene (as prepared in Referential Example 1) and 2.73 g of tetramethyl ammonium chloride, and reaction was carried out at 70° C. for 3 hours with stirring.

While this temperature was being maintained, 79 g of a 48% aqueous solution of sodium hydroxide (the molar ratio to the tris-phenol was 2.85) was continuously dropped to the reaction mixture over a period of 2 hours. The pressure in the system was reduced to 150 to 250 mmHg and water formed by the reaction was removed from the system, and epichlorohydrin azeotropically distilled was returned into the system. Even after the dropwise addition, water was removed from the system until formation of water was not observed. Subsequently, unreacted epichlorohydrin was removed from the reaction mixture by distillation. To the residue were added 230 g of methylisobutylketone and 230 g of water, and the mixture was stirred to transfer formed sodium chloride into the aqueous phase. Then, the mixture was allowed to stand still and the separated aqueous phase was removed.

Then, 20 g of a 24% aqueous solution of sodium hydroxide was added to the oil phase and the mixture was stirred at 90° C. for 2 hours to effect the second dehydrohalogenation. Then, the oil phase was separated from the aqueous phase and neutralized with 76 g of a 30% aqueous solution of sodium dihydrogenphosphate, and removal of water by azeotropic distillation and removal of the salt by filtration using 4G glass filter were carried out.

Methylisobutylketone was completely removed from the oil phase under a reduced pressure of 5 mmHg at 150° C. to obtain 180 g of 1-{α-methyl-α-(4'-glycidoxyphenyl)ethyl}-4-{α',α'-bis(4''-glycidoxyphenyl)ethyl} benzene having an epoxy equivalent of 219 and a softening point of 63° C. The infrared absorption spectrum of the obtained resin is shown in FIG. 1.

The results of $^1$H-NMR (proton nuclear magnetic resonance; CDCl$_3$ solution) are as follows:

$\delta$ = 1.62, 6H, s; 3.17–3.44, 3H, m; 2.07, 3H, s; 3.77–4.24, 6H, m; 2.64–2.94, 6H, m; 6.69–7.20, 16H, m.

EXAMPLE 2

Procedures of Example 1 were repeated in the same manner except that 155.0 g of 1-{α-methyl-α-(3',5'-dimethyl-4'-hydroxyphenyl)ethyl}-4-{α',α'-bis(3'',5''-dimethyl-4''-hydroxyphenyl)ethyl}benzene prepared in Referential Example 3 was used as the tris-phenol, whereby 196 g of 1-{α-methyl-α-(3',5'-dimethyl-4'-glycidoxyphenyl)ethyl}-4-{α',α'-bis(3'',5''-dimethyl-4''-glycidoxyphenyl)ethyl}benzene having an epoxy equivalent of 240 and a softening point of 87° C. was obtained. The infrared absorption spectrum of the obtained epoxy resin is shown in FIG. 2.

The results of $^1$H-NMR (proton nuclear magnetic resonance; CDCl$_3$ solution) are as follows:

$\delta$ = 1.62, 6H, s; 3.18–3.44, 3H, m; 2.06, 3H, s; 3.60–4.15, 6H, m; 2.17, 12H, s; 6.65, 4H, s; 2.21, 6H, s; 6,82, 2H, s; 2.61–2.95, 6H, m; 6.95–7.03, 4H, d.

APPLICATION EXAMPLE 1

A cured product was obtained by heating and mixing 100 parts (parts by weight; all of "parts" given hereinafter are by weight) of the epoxy resin obtained in Example 1 with 78 parts of Methyl Nadic anhydride (Kayahard MCD supplied by Nippon Kayaku) and 1 part of 2-ethyl-4-methylimidazole (2E4MZ supplied by Shikoku Kasei) at 100° C. for 3 hours and at 230° C. for 2 hours. The obtained cured product was tested with respect to the heat distortion temperature (ASTM D-648), the flexural strength (JIS K-6911) and the flexural modulus (JIS K-6911).

APPLICATION EXAMPLE 2

In the same manner as described in Application Example 1, a cured product was prepared from 50 parts of the epoxy resin obtained in Example 1, 50 parts of a bisphenol A type epoxy resin (EPOMIK R-140 supplied by Mitsui Sekiyu Kagaku), 84 parts of Methyl Nadic anhydride and 1 part of 2-ethyl-4-methylimidazole and the obtained cured product was tested.

APPLICATION EXAMPLE 3

In the same manner as described in Application Example 1, a cured product was prepared from 100 parts of the epoxy resin obtained in Example 2, 71 parts of Methyl Nadic anhydride and 1 part of 2-ethyl-4-methylimidazole and the cured product was tested.

COMPARATIVE APPLICATION EXAMPLE 1

In the same manner as described in Application Example 1, a cured product was prepared from 100 parts of a bisphenol A type epoxy resin (EPOMIK R-140), 90 parts of Methyl Nadic anhydride and 1 part of 2-ethyl-4-methylimidazole and the cured product was tested.

COMPARATIVE APPLICATION EXAMPLE 2

In the same manner as described in Application Example 1, a cured product was prepared from 100 parts of an o-cresol-novolak type epoxy resin (EOCN 102 supplied by Nippon Kayaku), 81 parts of Methyl Nadic anhydride and 1 part of 2-ethyl-4-methylimidazole and the cured product was tested.

The results obtained in the application examples and comparative application examples are shown in Table 1.

TABLE 1

| | Heat Distortion Temperature (° C.) | Flexural Strength (Kg/mm$^2$) | Flexural Modulus (Kg/mm$^2$) |
|---|---|---|---|
| Application Example 1 | 236 | 11.7 | 283 |
| Application Example 2 | 198 | 12.6 | 287 |
| Application Example 3 | 239 | 10.5 | 296 |
| Comparative Application Example 1 | 169 | 13.0 | 299 |
| Comparative Application Example 2 | 235 | 7.8 | 322 |

EXAMPLE 3

A 1-liter separable flask was charged with 400 g of 1-{α-methyl-α-(4'-glycidoxyphenyl)ethyl}-4-{α',α'-bis(4''-glycidoxyphenyl)ethyl}benzene (having an epoxy equivalent of 209), 176.4 g of tetrabromobisphenol A and 60 g of xylene, and 1.6 ml of an aqueous solution containing 1% by weight of tetramethyl ammonium chloride was further added. When the mixture was heated with stirring in a nitrogen gas atmosphere, the mixture became completely homogeneous at a temperature of up to 100° C. Then, the pressure was reduced and xylene and water were removed while elevating the temperature to 140° C. The pressure was returned to atmospheric pressure and the reaction mixture was further heated at 150° C. for 6 hours in a nitrogen gas atmosphere.

As a result, 576.4 g of an epoxy resin composition having an epoxy equivalent of 486 and a bromine content of about 18% by weight was obtained. This epoxy resin composition was soluble in methylethylketone.

EXAMPLE 4

Procedures of Example 3 were repeated in the same manner except that a mixture of 280 g of 1-{α-methyl-α-(4'-glycidoxyphenyl)ethyl}-4-{α',α'-bis(4''-glycidoxyphenyl)ethyl}benzene (having an epoxy equivalent of 217) and 120 g of a bisphenol A type epoxy resin (having an epoxy equivalent of 189; EPOMIK R-140 supplied by Mitsui Sekiyu Kagaku) was used instead of 400 g of 1{α-methyl-α-(4'-glycidoxyphenyl)ethyl}-4-{α',α'-bis(4''-glycidoxyphenyl)ethyl}benzene, whereby 576.4 g of an epoxy resin composition having an epoxy equivalent of 453 and a bromine content of about 18% by weight was obtained. This epoxy resin composition was soluble in methylethylketone.

EXAMPLE 5

Procedures of Example 3 were repeated in the same manner except that 400 g of 1-{α-methyl-α-(3',5'-dimethyl-4'-glycidoxyphenyl)ethyl}-4-{α',α'-bis(3'',5''-dimethyl-4''-glycidoxyphenyl)ethyl}benzene (having an epoxy equivalent of 240) was used instead of 400 g of 1-{α-methyl-α-(4'-glycidoxyphenyl)-ethyl}-4-{α',α'-bis(4''-glycidoxyphenyl)ethyl}benzene, whereby 576.4 g of an epoxy resin composition having an epoxy equivalent of 451 and a bromine content of about 18% by weight was obtained. This epoxy resin composition was soluble in methylethylketone.

COMPARATIVE EXAMPLE 1

Procedures of Example 3 were repeated in the same manner except that 400 g of an o-cresol-novolak type epoxy resin (having an epoxy equivalent of 212; EOCN 102 supplied by Nippon Kayaku) was used instead of 400 g of 1-{α-methyl-α-(4'-glycidoxyphenyl)ethyl}-4-{α',α'-bis(4''-glycidoxyphenyl)ethyl}benzene. When the reaction was conducted for several hours, the reaction product was gelled, and the obtained reaction product was insoluble in methylethylketone.

APPLICATION EXAMPLE 4

The epoxy resin composition obtained in Example 3 was dissolved in methylethylketone to form a solution having an epoxy resin concentration of 75% by weight. This epoxy resin solution (100 parts by weight as the solid) was mixed with a solution comprising 15 parts by weight of methyl Cellosolve, 15 parts by weight of dimethylformamide, 3.1 parts by weight of dicyandiamide and 0.2 part by weight of 2-ethyl-4-methylimidazole (2E4MZ supplied by Shikoku Kasei) to form a varnish-like epoxy resin composition.

A glass cloth (WE-18K-EZ2 supplied by Nitto Boseki) was impregnated with this composition and was heated at 150° C. for 6 minutes to obtain a prepreg of the B stage having a resin impregnation ratio of about 45% by weight. These prepregs were piled in 9 plies and a glass cloth laminated plate was formed under molding conditions of 180° C., 10 Kgf/cm² and 90 minutes.

The glass transition temperature (Tg) of the cured resin of the obtained laminated plate was 170° C. as measured by a differential scanning calorimeter (DSC), and the flame retardancy was 94V-O as determined by the UL method.

APPLICATION EXAMPLE 5

A glass cloth laminated plate was prepared by repeating procedures of Application Example 4 in the same manner except that the epoxy resin composition obtained in Example 4 was used instead of the epoxy resin composition obtained in Example 3 and the amount used of dicyandimide was changed to 4.2 parts by weight.

Tg of the cured resin of the laminate plate was 175° C., and the flame retardancy was 94V-O as determined by the UL method.

COMPARATIVE APPLICATION EXAMPLE 3

A glass cloth laminated plate was prepared by repeating procedures of Application Example 4 in the same manner except the 100 parts by weight of a brominated bisphenol A type epoxy resin (having an epoxy equivalent of 408 and a bromine content of 18% by weight) was used instead of the epoxy resin composition obtained in Example 3 and the amount used of dicyandiamide was changed 4.7 parts by weight.

Tg of the cured resin of the laminated plate was 127° C.

APPLICATION EXAMPLE 6

A glass cloth laminated plate was prepared by repeating procedures of Application Example 4 in the same manner except that the epoxy resin composition obtained in Example 5 was used instead of the epoxy resin composition obtained in Example 3 and the amount used of dicyandiamide was changed to 4.2 parts by weight.

Tg of the cured resin of the laminate plate was 190° C. and the flame retardancy was 94V-O as determined by the UL method.

COMPARATIVE APPLICATION EXAMPLE 4

A glass cloth laminated plate was prepared by repeating procedures of Application Example 4 in the same manner except that a mixture (having a bromine content of about 18% by weight) comprising 86 parts by weight of a brominated bisphenol A type epoxy resin (having an epoxy equivalent of 479 and a bromine content of 21% by weight) and 14 parts by weight of an o-cresol-novolak type epoxy resin (having an epoxy equivalent of 210; EOCN 103S supplied by Nippon Kayaku) was used instead of the epoxy resin composition obtained in Example 3.

Tg of the cured resin of the laminated plate was 137° C.

What is claimed is:

1. A heat-resistant flame-retardant epoxy resin composition comprising a halogen-containing epoxy resin obtained by reacting (A) a trifunctional epoxy compound represented by the following general formula (I):

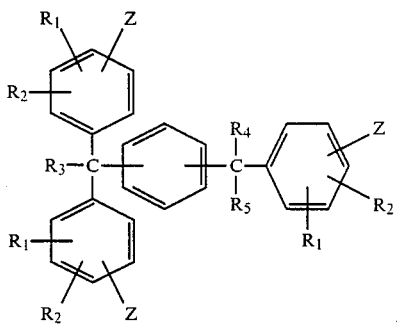 (I)

wherein $R_1$ and $R_2$ stand for a hydrogen atom, an alkyl group having 1 to 12 carbon atoms, an aryl group or a cycloalkyl group having 3 to 6 carbon atoms, $R_3$ stands for a hydrogen atom or an alkyl group having 1 to 10 carbon atoms, $R_4$ and $R_5$, independently, stand for a hydrogen atom or an alkyl group having 1 to 4 carbon atoms and Z stands for a group represented by the following general formula (II):

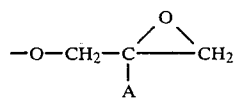 (II)

in which A stands for a hydrogen atom or a methyl group,
or a combination of said trifunctional epoxy compound and a difunctional epoxy compound obtained by condensation of a bisphenol with an epihalohydrin with (B) a halogenated bisphenol in the presence of a catalyst.

2. A composition as set forth in claim 1 wherein the halogen-containing epoxy resin has an epoxy equivalent of 200 to 2,000.

3. A composition as set forth in claim 1 wherein the halogen-containing epoxy resin has a halogen content of 5 to 30% by weight.

4. A composition as set forth in claim 1 wherein the halogenated bisphenol is tetrabromobisphenol A.

5. A composition as set forth in claim 1 wherein the trifunctional epoxy compound is a compound represented by the following general formula (XIII):

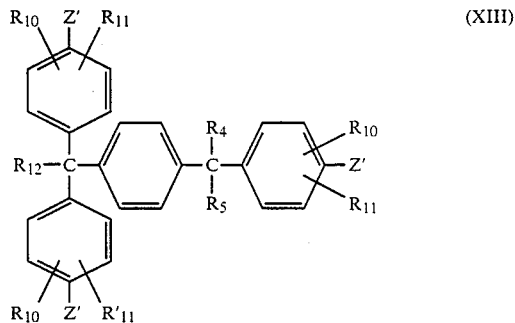 (XIII)

wherein Z' stands for a glycidoxy group, and $R_{10}$, $R_{11}$, $R_{12}$, $R_4$ and $R_5$, each independently, stand for a hydrogen atom or an alkyl group having 1 to 4 carbon atoms.

6. A composition as set forth in claim 1 wherein the trifunctional epoxy compound is 1-{α-methyl-α-(4'-glycidoxyphenyl)ethyl}-4-{α',α'-bis(4''-glycidoxyphenyl)ethyl}benzene.

7. A composition as set forth in claim 1 wherein the trifunctional epoxy compound is 1-{α-methyl-α-(3',5'-dimethyl-4'-glycidoxyphenyl)ethyl}-4'-{α',α'-bis(3'',5''-dimethyl-4''-glycidoxyphenyl)ethyl}benzene.

8. A composition as set forth in claim 1 wherein the weight ratio of the trifunctional epoxy compound to the difunctional epoxy compound is in the range of from 50/50 to 90/10.

9. A composition as set forth in claim 1 wherein the weight ratio of the trifunctional epoxy compound to the difunctional epoxy compound is in the range of from 60/40 to 80/20.

10. A composition as set forth in claim 1 which is soluble in methylethylketone.

11. A heat-resistant flame-retardant epoxy resin composition comprising a halogen-containing epoxy resin represented by the following general formula (XVI):

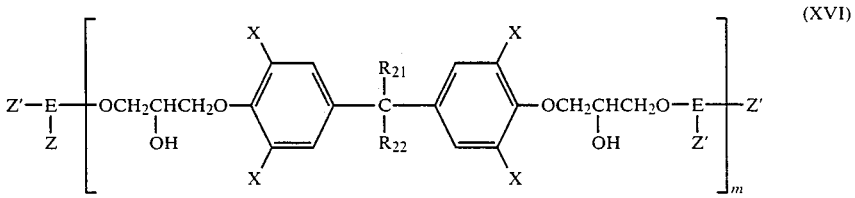 (XVI)

wherein Z' stands for a glycidoxy group, $R_{21}$ and $R_{22}$ stand for a hydrogen atom or an alkyl group having 1 to 4 carbon atoms, X stands for a halogen atom, E stands for a group represented by the following formula (XIII'):

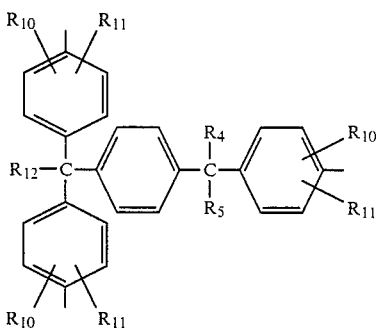

in which $R_{10}$, $R_{11}$, $R_{12}$, $R_4$ and $R_5$, each independently, stand for a hydrogen atom or an alkyl group having 1 to 4 carbon atoms, and m is an integer of at least 1, said halogen-containing epoxy resin having an epoxy equivalent of 300 to 2,000 and a halogen content of 5 to 30% by weight.

12. A heat-resistant flame-retardant epoxy resin composition comprising a halogen-containing epoxy resin represented by the following general formula (XVII):

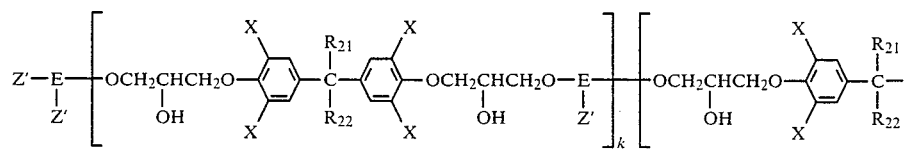

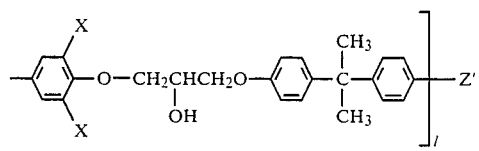

wherein Z' stands for glycidoxy group, $R_{21}$ and $R_{22}$ stand for a hydrogen atom or an alkyl group having 1 to 4 carbon atoms, X stands for a halogen atom, E stands for a group represented by the following formula (XIII'):

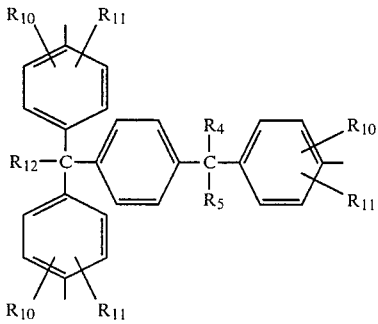

in which $R_{10}$, $R_{11}$, $R_{12}$, $R_4$ and $R_5$, each independently, stand for a hydrogen atom or an alkyl group having 1 to 4 carbon atoms, k is 0 or an integer of at least 1, l is an integer of at least 1, and k and l are selected so that the halogen-containing epoxy resin has an epoxy equivalent of 300 to 2,000 and a halogen content of 5 to 30% by weight.

13. A trifunctional epoxy resin represented by the following general formula (IX):

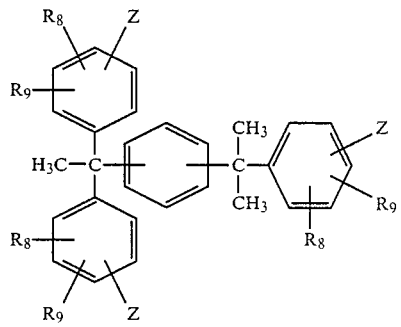

wherein $R_8$ and $R_9$ stand for a hydrogen atom, a halogen atom, a lower alkyl group having 1 to 4 carbon atoms or a lower alkoxy group having 1 to 4 carbon atoms, the groups $R_8$ and $R_9$ bonded to the respective phenyl groups may be the same or different, and Z stands for a group represented by the following general formula (II):

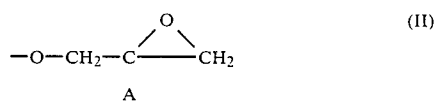

in which A stands for a hydrogen atom or a methyl group.

14. 1-{α-methyl-α-(4'-glycidoxyphenyl)ethyl}-4-}α'-,α'-bis(4''-glycidoxyphenyl)ethyl}benzene.

15. 1-{α-methyl-α-(3',5'-dimethyl-4'-glycidoxyphenyl)ethyl}-4-{α',α'-bis(4''-glycidoxyphenyl)ethyl}benzene.

* * * * *

UNITED STATES PATENT AND TRADEMARK OFFICE
CERTIFICATE OF CORRECTION

PATENT NO. : 4,954,603

DATED : September 4, 1990

INVENTOR(S) : Toshimasa TAKATA, and Kenichi MIZUNO

It is certified that error appears in the above-identified patent and that said Letters Patent is hereby corrected as shown below:

On the title page, item [30]:
Under "Foreign Application Priority Data", change

" Oct. 8, 1985 [JP] Japan.................60-224305
  Dec. 20, 1985 [JP] Japan.................60-237288"

to

-- Oct. 8, 1985 [JP] Japan.................60-224305
   Dec. 20, 1985 [JP] Japan.................60-287288
   June 24, 1986 [JP] Japan.................61-147808
   Dec. 24, 1986 [JP] Japan.................61-306561 --.

Signed and Sealed this

Twenty-fifth Day of August, 1992

Attest:

DOUGLAS B. COMER

*Attesting Officer*          *Acting Commissioner of Patents and Trademarks*